US00PP16212P2

(12) United States Plant Patent
Smith

(10) Patent No.: US PP16,212 P2
(45) Date of Patent: Jan. 24, 2006

(54) ***CHRYSANTHEMUM* PLANT NAMED 'SWEET YOJEANETTE'**

(50) Latin Name: *Chrysanthemum×morifolium*
Varietal Denomination: Sweet Yojeanette

(75) Inventor: Mark A. Smith, Fort Myers, FL (US)

(73) Assignee: Yoder Brothers, Inc., Barberton, OH (US)

( * ) Notice: Subject to any disclaimer, the term of this patent is extended or adjusted under 35 U.S.C. 154(b) by 118 days.

(21) Appl. No.: 10/764,880

(22) Filed: Jan. 26, 2004

(51) Int. Cl.
*A01H 5/00* (2006.01)

(52) U.S. Cl. ..... Plt./294

(58) Field of Classification Search ..... Plt./294, Plt./295

See application file for complete search history.

*Primary Examiner*—Howard J. Locker
(74) *Attorney, Agent, or Firm*—C. A. Whealy

(57) ABSTRACT

A new and distinct cultivar of *Chrysanthemum* plant named 'Sweet Yojeanette', characterized by its upright and outwardly spreading plant habit; freely branching habit; dense and full plant habit; uniform and freely flowering habit; daisy-type inflorescences with elongated oblong-shaped ray florets; creamy white-colored ray florets and bright yellow-colored disc florets; and natural season flowering in early October in the Northern Hemisphere.

2 Drawing Sheets

Botanical classification/cultivar designation: *Chrysanthemum×morifolium* cultivar Sweet Yojeanette.

BACKGROUND OF THE INVENTION

The present invention relates to a new and disctinct cultivar of *Chrysanthemum* plant, botanically known as *Chrysanthemum×morifolium*, commercially known as a garden-type *Chrysanthemum* and hereinafter referred to by the name 'Sweet Yojeanette'.

The new cultivar is a product of a planned breeding program conducted by the Inventor in Alva, Fla. The objective of the breeding program is to create new garden-type *Chrysanthemum* cultivars having inflorescences with desirable inflorescence forms, attractive floret colors and good garden performance.

The new *Chrysanthemum* is a naturally-occurring whole plant mutation of the *Chrysanthemum×morifolium* cultivar Yojeanette, disclosed in U.S. Plant Pat. No. 13,908. The new *Chrysanthemum* was discovered and selected by the Inventor as a single flowering plant from within a population of plants of the cultivar Yojeanette in a controlled environment in Alva, Fla. in April, 2002. The selection of this plant was based on its desirable inflorescence form, attractive ray floret color and good garden performance.

Asexual reproduction of the new cultivar by terminal vegetative cuttings taken in a controlled environment in Alva, Fla. since June, 2002, has shown that the unique features of this new *Chrysanthemum* are stable and reproduced true to type in successive generations.

SUMMARY OF THE INVENTION

The cultivar Sweet Yojeanette has not been observed under all possible environmental conditions. The phenotype may vary somewhat with variations in environment such as temperature, daylength and light intensity, without, however, any variance in gentoype.

The following traits have been repeatedly observed and are determined to be the unique characteristics of 'Sweet Yojeanette'. These characteristics in combination distinguish 'Sweet Yojeanette' as a new and distinct cultivar:

1. Upright and outwardly spreading plant habit.
2. Freely branching habit; dense and full plants.
3. Uniform and freely flowering habit.
4. Daisy-type inflorescences with elongated oblong-shaped ray florets.
5. Creamy white-colored ray florets and bright yellow-colored disc florets.
6. Natural season flowering in early October in the Northern Hemisphere.

In side-by-side comparisons conducted in Alva, Fla., plants of the new *Chrysanthemum* differed from plants of the parent, the cultivar Yojeanette in the following characteristics:

1. Plants of the new *Chrysanthemum* flowered one day later than plants of the cultivar Yojeanette when grown under natural season conditions.
2. Plants of the new *Chrysanthemum* and the cultivar Yojeanette differed in ray floret coloration as plants of the cultivar Yojeanette had light pink-colored ray florets.

Plants of the new *Chrysanthemum* can be compared to plants of the *Chrysanthemum* cultivar Tracy, disclosed in U.S. Plant Pat. No. 8,609. In side-by-side comparisons conducted in Alva, Fla., plants of the new *Chrysanthemum* differed from plants of the cultivar Tracy in the following characteristics:

1. Plants of the new *Chrysanthemum* were larger and more rounded than plants of the cultivar Tracy.
2. Plants of the new *Chrysanthemum* flowered about one week later than plants of the cultivar Tracy when grown under natural season conditions.

Plants of the new *Chrysanthemum* can be compared to plants of the *Chrysanthemum* cultivar Pidoul, disclosed in U.S. Plant Pat. No. 10,218. In side-by-side comparisons conducted in Alva, Fla., plants of the new *Chrysanthemum* differed from plants of the cultivar Pidoul in the following characteristics:

1. Plants of the new *Chrysanthemum* had larger inflorescences than plants of the cultivar Pidoul.
2. Plants of the new *Chrysanthemum* flowered about two weeks earliear than plants of the cultivar Pidoul when grown under artificial short day/long night photoperiodic conditions.
3. Ray florets of plants of the new *Chrysanthemum* maintained the creamy white coloration for ten days longer than ray florets of plants of the cultivar Pidoul.

BRIEF DESCRIPTION OF THE PHOTOGRAPHS

The accompanying photographs illustrate the overall appearance of the new *Chrysanthemum*. These photographs show the colors as true as it is reasonably possible to obtain in colored reproductions of this type. Colors in the photographs may differ slightly from the color values cited in the detailed botanical description which accurately describe the colors of the new *Chrysanthemum*.

The photograph on the first sheet comprises a side perspective view of a typical flowering plant of 'Sweet Yojeanette' grown in a container.

The photograph on the second sheet comprises a close-up view of a typical inflorescences of the cultivar 'Sweet Yojeanette'.

DETAILED BOTANICAL DESCRIPTION

In the following description, color references are made to The Royal Horticultural Society Colour Chart, 1995 Edition, except where general terms of ordinary dictionary significance are used. The following observations and measurements describe plants grown in Alva, Fla. during the winter in a fiberglass-covered greenhouse under conditions and practices which approximate those generally used in commercial garden-type *Chrysanthemum* production. One cutting was planted in a 15.25-cm container in early December, 2002. Plants were pinched one time, that is, the terminal apex was removed to enhance branching, at the end of December. One week after the pinch, plants were exposed to short day/long night photoperiodic treatments until flowering. During the production of the plants, day temperatures averaged 26° C. and night averaged 18° C. Measurements and numerical values represent averages for typical flowering plants.

Botanical classification: *Chrysanthemum×morifolium* cultivar Sweet Yojeanette.

Commercial classification: Daisy-type garden *Chrysanthemum*.

Parentage: Naturally-occurring whole plant mutation of the *Chrysanthemum×morifolium* cultivar Yojeanette, disclosed in U.S. Plant Pat. No. 13,908.

Propagation:

*Type.*—Terminal vegetative cuttings.

*Time to initiate roots.*—About four days at 21° C.

*Time to produce a rooted cutting.*—About ten to twelve days at 21° C.

*Root description.*—Fine, fibrous; white in color.

*Rooting habit.*—Freely branching.

Plant description:

*Plant form/growth habit.*—Perennial herbaceous daisy-type garden *Chrysanthemum*. Inverted triangle with mounded crown. Stems initially upright, then outwardly spreading. Freely branching with about ten lateral branches per plant. Moderately vigorous to vigorous.

*Plant height.*—About 16 cm.

*Plant diameter.*—About 23 cm.

*Lateral branches.*—Length: About 14.5 cm. Diameter: About 2 mm. Internode length: About 1.3 cm. Aspect: Upright and outwardly spreading. Texture: Pubescent. Color: 146A.

*Foliage description.*—Leaf arrangement: Alternate. Length: About 3.75 cm. Width: About 3.3 cm. Apex: Mucronate. Base: Truncate. Margin: Palmately lobed, sinuses parallel to divergent. Texture, upper surface: Slightly pubescent. Texture, lower surface: Pubescent; veins prominent. Color: Developing and fully expanded foliage, upper surface: Slightly darker than 147A. Developing and fully expanded foliage, lower surface: 147B. Venation, upper surface: 147A. Venation, lower surface: Close to 147B. Petiole length: About 1.7 cm. Petiole diameter: About 1 mm. Petiole color, upper surface: 147A to 147B. Petiole color, lower surface: 147B.

Inflorescence description:

*Appearance.*—Daisy-type inflorescence form with elongated oblong-shaped ray florets. Inflorescences borne on terminals above foliage, arising from leaf axils. Disc and ray florets developing acropetally on a capitulum. About seven to eight inflorescences per lateral branch.

*Flowering response.*—Under natural season conditions, plants flower in early October in the Northern Hemisphere.

*Inflorescence bud (before showing color).*—Height: About 3.5 mm. Diameter: About 5 mm. Shape: Oblate. Color (lower surface of phyllaries): More green than 147A.

*Inflorescence size.*—Diameter: About 3.5 cm. Depth (height): About 8 mm. Disc diameter: About 7.5 mm. Receptacle diameter: About 2 mm.

*Ray florets.*—Shape: Elongated oblong. Length: About 1.7 cm. Corolla tube length: About 1 mm. Width: About 3 mm. Apex: Rounded or emarginate. Margin: Fused. Texture: Smooth, glabrous; satiny. Surface: Mostly flat. Orientation: Initially upright, then perpendicular to vertical. Number of ray florets per inflorescence: About 28 in about two whorls. Color: When opening and fully opened, upper surface: Slightly more yellow than 155D. When opening and fully opened, lower surface: Slightly more yellow than 155D.

*Disc florets.*—Shape: Tubular; apex dentate, five-pointed. Length: About 3.75 mm. Width, apex: About 1 mm. Width, base: Less than 1 mm. Number of disc florets per inflorescence: About 54. Color: Immature: Close to 154A. Mature: Apex: Close to 9A. Mid-section: Close to 144D. Base: Close to 155D.

*Phyllaries.*—Quantity per inflorescence: About 18. Length: About 3.5 mm. Width: About 1 mm. Shape: Lanceolate. Apex: Acute. Base: Truncate. Margin: Entire. Texture, upper surface: Smooth, waxy. Texture, lower surface: Pubescent. Color, upper surface: Close to 147A. Color, lower surface: More green than 147A.

*Peduncle.*—Length: First peduncle: About 2.75 cm. Fourth peduncle: About 2.8 cm. Seventh peduncle: About 2.9 cm. Diameter: Less than 1 mm. Strength: Strong. Aspect: About 45° from vertical. Texture: Pubescent. Color: 146A.

*Reproductive organs.*—Androecium: Present on disc florets only. Anther color: 9A. Pollen: None observed. Gynoecium: Present on both ray and disc florets.

*Seed/fruit.*—Seed and fruit production has not been observed.

Disease/pest resistance: Plants of the new *Chrysanthemum* have not been shown to be resistant to pathogens and pests common to *Chrysanthemums.*

Garden performance: Plants of the new *Chrysanthemum* have been observed to be tolerant to rain, wind and temperatures ranging from 0 to more than 38° C.

It is claimed:

1. A new and distinct cultivar of *Chrysanthemum* plant named 'Sweet Yojeanette', as illustrated and described.

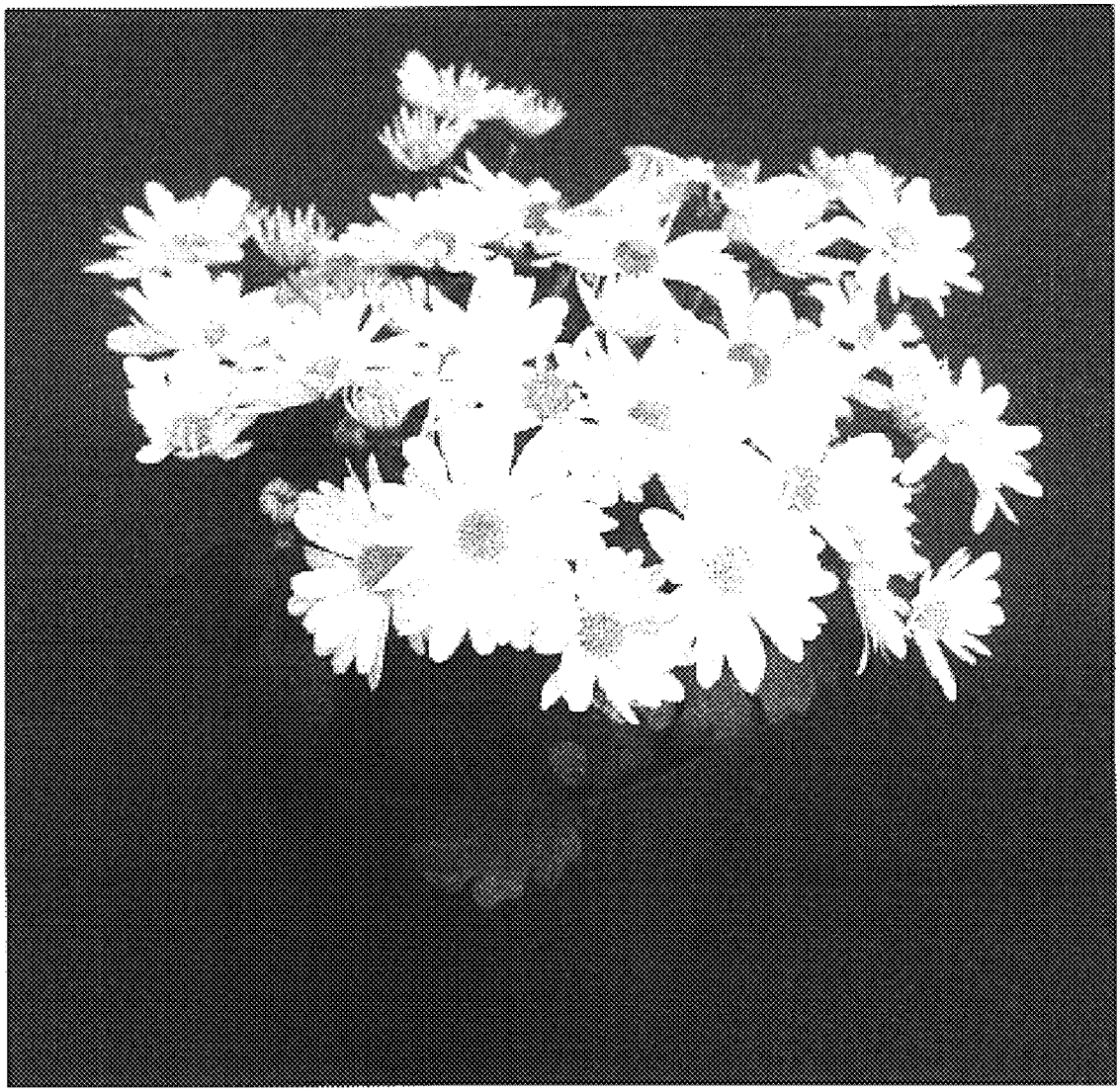

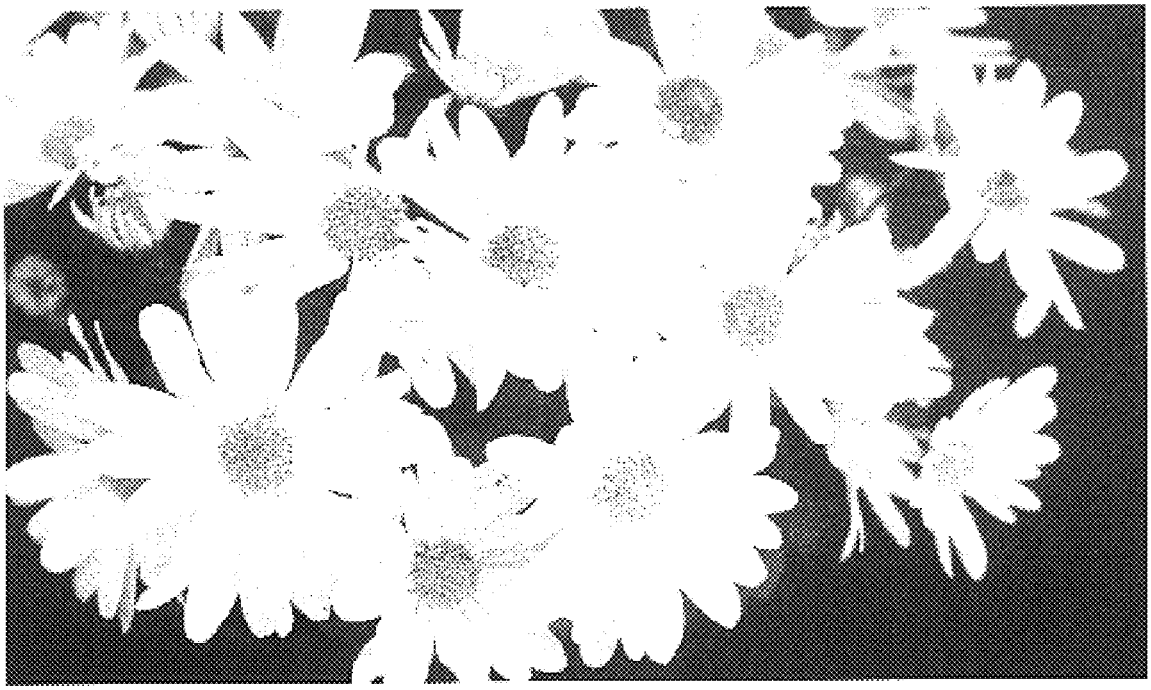

* * * * *